United States Patent [19]
Bruder et al.

[11] Patent Number: 5,258,917
[45] Date of Patent: Nov. 2, 1993

[54] METHOD FOR NESTING CONTOURS TO BE CUT OUT OF NATURAL LEATHER

[75] Inventors: Wolfgang Bruder, Bielefeld; Gerd Kupper, Salzuflen, both of Fed. Rep. of Germany

[73] Assignee: Durkopp Systemtechnik GmbH, Fed. Rep. of Germany

[21] Appl. No.: 688,908

[22] Filed: Apr. 19, 1991

[30] Foreign Application Priority Data

Apr. 19, 1990 [DE] Fed. Rep. of Germany ....... 4012462

[51] Int. Cl.$^5$ .............................................. G06F 15/46
[52] U.S. Cl. ................... 364/474.13; 364/470; 364/507; 382/8; 83/939
[58] Field of Search ................... 364/470, 468, 474.13, 364/474.09, 507; 382/1, 8; 83/76.8, 371, 936–941; 358/101, 106, 107; 250/562, 563, 572; 356/429–431, 237–239

[56] References Cited

U.S. PATENT DOCUMENTS

| | | | |
|---|---|---|---|
| 4,583,181 | 4/1986 | Gerber et al. | 364/470 |
| 4,725,961 | 2/1988 | Pearl | 364/474.13 |
| 4,739,487 | 4/1988 | Bonnet et al. | 364/470 |
| 4,901,359 | 2/1990 | Bruder | 382/8 |
| 4,941,183 | 7/1990 | Bruder et al. | 382/8 |
| 4,982,437 | 1/1991 | Loriot | 382/8 |
| 5,068,799 | 11/1991 | Jarrett, Jr. | 364/507 |
| 5,089,971 | 2/1992 | Gerber | 364/470 |

FOREIGN PATENT DOCUMENTS

| | | |
|---|---|---|
| 0277066A1 | 3/1983 | European Pat. Off. |
| 0277066 | 8/1988 | European Pat. Off. |
| 3519806 | 8/1988 | Fed. Rep. of Germany |
| 2548077 | 1/1985 | France |
| 8606676 | 11/1986 | PCT Int'l Appl. |
| 2143423 | 2/1985 | United Kingdom |

OTHER PUBLICATIONS

IEEE Transactions on Pattern Analysis and Machine Intelligence vol. PAMI-5, No. 6, Nov. 1983, Conners et al., pp. 573–583.
Leslie, "Automated Water Jet Cutting", *Mechanical Engineering*, vol. 98, No. 12, Dec. 1976, at 40–44.
Kodak Megaplus TM Camera published prior to Apr. 19, 1991.

*Primary Examiner*—Jerry Smith
*Assistant Examiner*—Steven R. Garland
*Attorney, Agent, or Firm*—Ostrolenk, Faber, Gerb & Soffen

[57] ABSTRACT

A completely automatic method for the nesting of contours to be cut from a piece of natural leather in which defects in structure and material as well as the outer contours of the leather are detected by means of a camera. The defective places, characterized by different shades of color, are transmitted to the electronic control unit. Pattern contours to be cut are stored in the electronic control unit, and regions wherein specific degrees of defect are tolerable are defined for each contour. A specific shade of color corresponds to each degree of defect, so that defects of the same degree are characterized by the same shade of color (in the case of black-and-white cameras by the same gray values; in the case of color cameras by the same color temperature). An automatic nesting simulation process is then effected via a software program. The pattern contours stored in the electronic control unit are electronically placed together with due consideration of the predetermined defect constraints and thus different cutting patterns are simulated. When an optimum cutting pattern has been found, i.e., the maximum possible degree of utilization has been obtained, the simulation image is stored and used later for controlling the automatic cutting system.

11 Claims, 6 Drawing Sheets

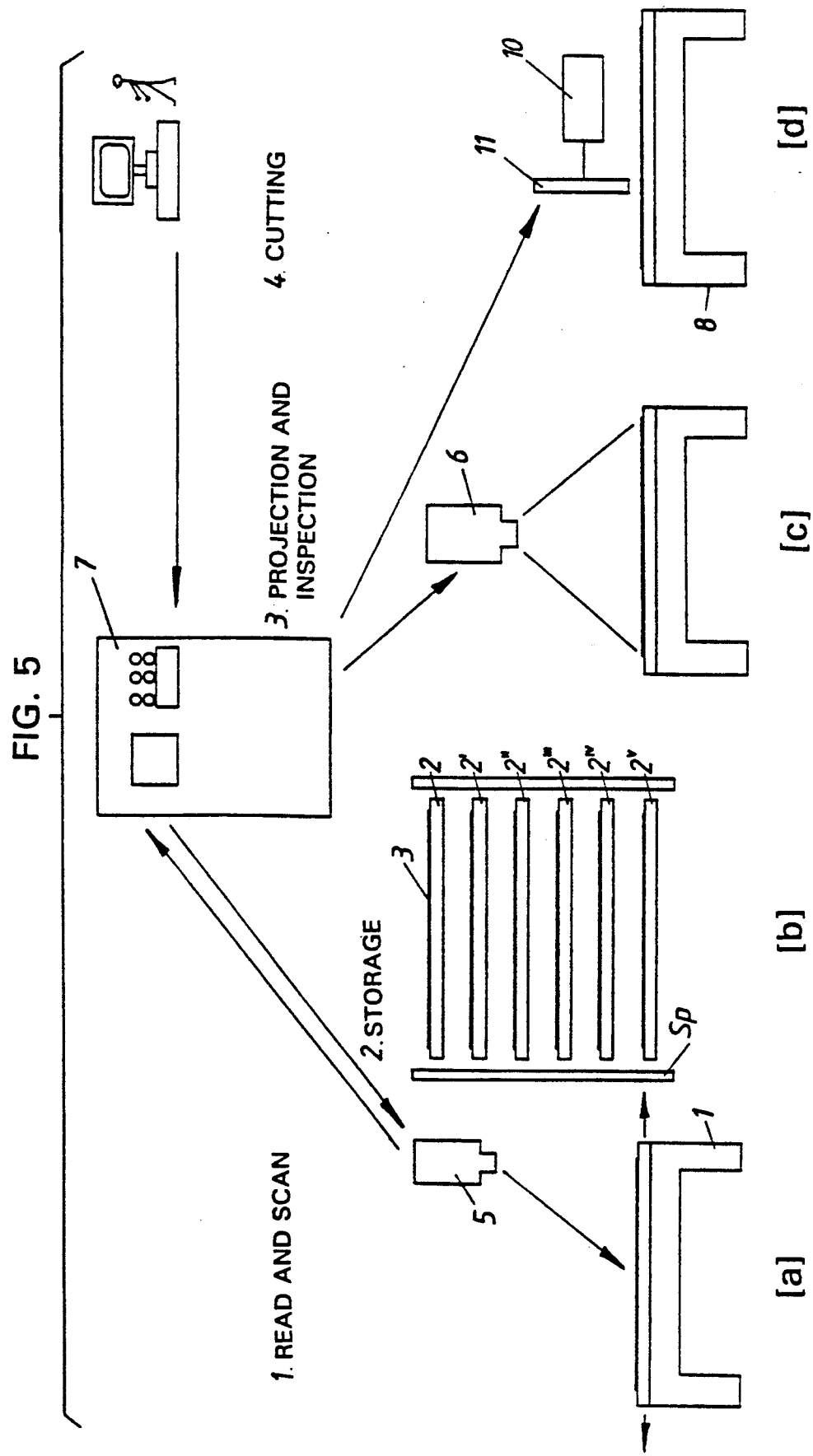

METHOD FOR NESTING CONTOURS TO BE CUT OUT OF NATURAL LEATHER

BACKGROUND OF THE INVENTION

1. Field of the Invention

The present invention relates to a method of optimally nesting the contours of parts to be cut out of a piece of natural leather.

2. Background Art

Various known methods serve for optimizing the cutting out of material and are characterized by the fact that the manual method steps are greatly simplified. See, for example, Federal Republic of Germany Patent 36 27 110 which is equivalent to U.S. Pat. No. 4,941,183. For this purpose, the contours which are to be cut from a flexurally limp material such as leather are not determined by direct application of stencils on the material, but rather the contours are projected onto the material to be cut. This can be done, for example, by scaling the stencils down in size and placing them on a projection table, and projecting the contours to be cut onto the material via a system of reflecting mirrors Furthermore, it is possible to provide an electronic projection unit by means of which contours which are stored in digital form in a computer can be projected directly onto the material to be cut. With these materials, the operator entrusted with the nesting can, in an interactive process, locate the projected contours with due consideration of defective places in the material to be cut.

For further automating the nesting process, particularly for natural leather, it is known from EP OS 0 277 066 to mark the defective places in the leather and to have them processed directly under the control of the cutting system. For this purpose, the defects are marked by the operator by fluorescent means. Then the marked places are detected by a camera and transmitted to a computer system which is provided with a stamping program for stamping out a given set of contours. The detected markings are interpreted by the computer system and are suitably taken into consideration as constraints upon the stamping program, so that the prescribed contours can then be stamped out automatically without defects being present in the material at places which cannot be tolerated. For this purpose, different markings are used by the operator for different qualities of defects, and these different markings can then be taken into consideration later on.

The disclosures of these and all other prior art mentioned herein are incorporated by reference.

SUMMARY OF THE INVENTION

Proceeding from this prior art, the central object of the present invention is to develop a method for nesting contours to be cut out of natural leather which can be carried out without requiring any manual steps, from the initial detection of the defects in the leather, up to the final cutting step.

This object may be achieved by a method for nesting contours to be cut out of a piece of natural leather comprising the steps of:

optically detecting the locations and sizes of any defects of the leather with an optical detection system, such defects being represented by the detection system in the form of varying detected shades of color;

transmitting data representative of such defects to a computer and storing such data therein;

storing a plurality of contours corresponding to parts to be cut out of said leather in the computer;

correlating the detected defect-representing shades with respective predefined degrees of said defects;

defining regions in the stored contours of the parts to be cut out, said regions having respective degree-of-defect ranges, which specify a maximum degree of defect to be accepted in each said region;

simulating a plurality of possible arrangements of the contours to be cut out in the computer, wherein in each possible arrangement, only defects within the permissible degree of defect range are present in said defined regions;

for each simulated arrangement, determining a degree of utilization of said skin;

comparing the degrees of utilization of said simulated arrangements; and after completing the comparison, automatically cutting according to the arrangement with which an optimal degree of utilization has been obtained.

It may be advantageous also to detect the outer contour of the skin to be cut. It may not be necessary in some contexts to detect the sizes of the defects.

The locations of the defects in the structure or material of the leather are detected by the camera or optical device as a function of the degree of the defect, which is correlated in turn to different shades of detected color. Regions corresponding to a given shade or color corresponding to a given degree of defect may be associated with the contours to be cut out, and stored in the control unit, whereby an automatic comparison can be effected as to whether the contours to be cut later on will contain only defects which can be tolerated.

By this feature, it is assured that defects which are actually present in the material will be disregarded if they will be located subsequently at an invisible or non-disturbing place on the finished part. Thus, for instance, a scar in the leather which will subsequently be on the bottom of the finished part can be tolerated while a hole cannot. As another example, a small hole may be tolerable, but not a large hole.

Since the computer can rapidly simulate all possible arrangements of contours, an optimal result is thereby obtained. If each individual skin is scanned initially, then a cutting program can be established and stored individually for each skin. In this way, the nesting can be optimized over a very large number of skins which can be placed in a goods storage area until they are ready to be used, for a very efficient cutting process. Since each skin then has a given cutting program associated with it, the nesting process and the cutting process can be separated from each other by a period of time which is as long as desired.

Due to the fact that a very large number of skins can be processed before any are cut, the degree of utilization can be optimized over a correspondingly large number of skins. In other words, for a predetermined cutting pattern, not only is the best possible degree of utilization of an individual skin strived for, but also the optimizing is extended to a day's, week's or month's production of a cutting plant.

The method of the invention may further comprise the steps of defining edge associations of the contours with respect to each other, and taking such edge associations into account when determining said possible arrangements. In this connection, the courses of edges of adjacent contours to be cut out may be matched so as to reduce waste of leather material between said contours Alternatively or in addition, grain patterns of said skin within said contours may be matched so as to achieve an aesthetically improved transition between said contours. By these features, it is possible for two different contours which abut at a visible place in the finished part to be so selected so that the transitions are less visible.

The optical detection system may include a black-and-white camera or a color camera.

Advantageously, with increasing degree of defect, colors of correspondingly higher color temperatures may be recorded by the camera. When a color camera is used, it is possible to grade the individual degrees of defects more precisely and provide additional criteria to optimize the nesting process.

According to a further advantageous feature, colors of higher temperature may be defined to include all colors of lower temperature so that an acceptance range ($Gmax > G4 > G3 > \ldots > G1$) of degrees of defect ($FG1, \ldots, FGmax$) is created, the acceptance range ($Gn$) permissible in each case including all lower and equal degrees of the detected defects ($FG1, \ldots, FGn-1; FGn$)

In addition to the cameras mentioned above, the optical detection system may include a laser scanner which detects the outer contour and/or the defects.

BRIEF DESCRIPTION OF THE DRAWINGS

Other objects, features and advantages of the present invention will become apparent from the following detailed description of embodiments of the invention, with reference to the accompanying drawings, in which.

DETAILED DESCRIPTION OF THE DRAWINGS

Figure 1:
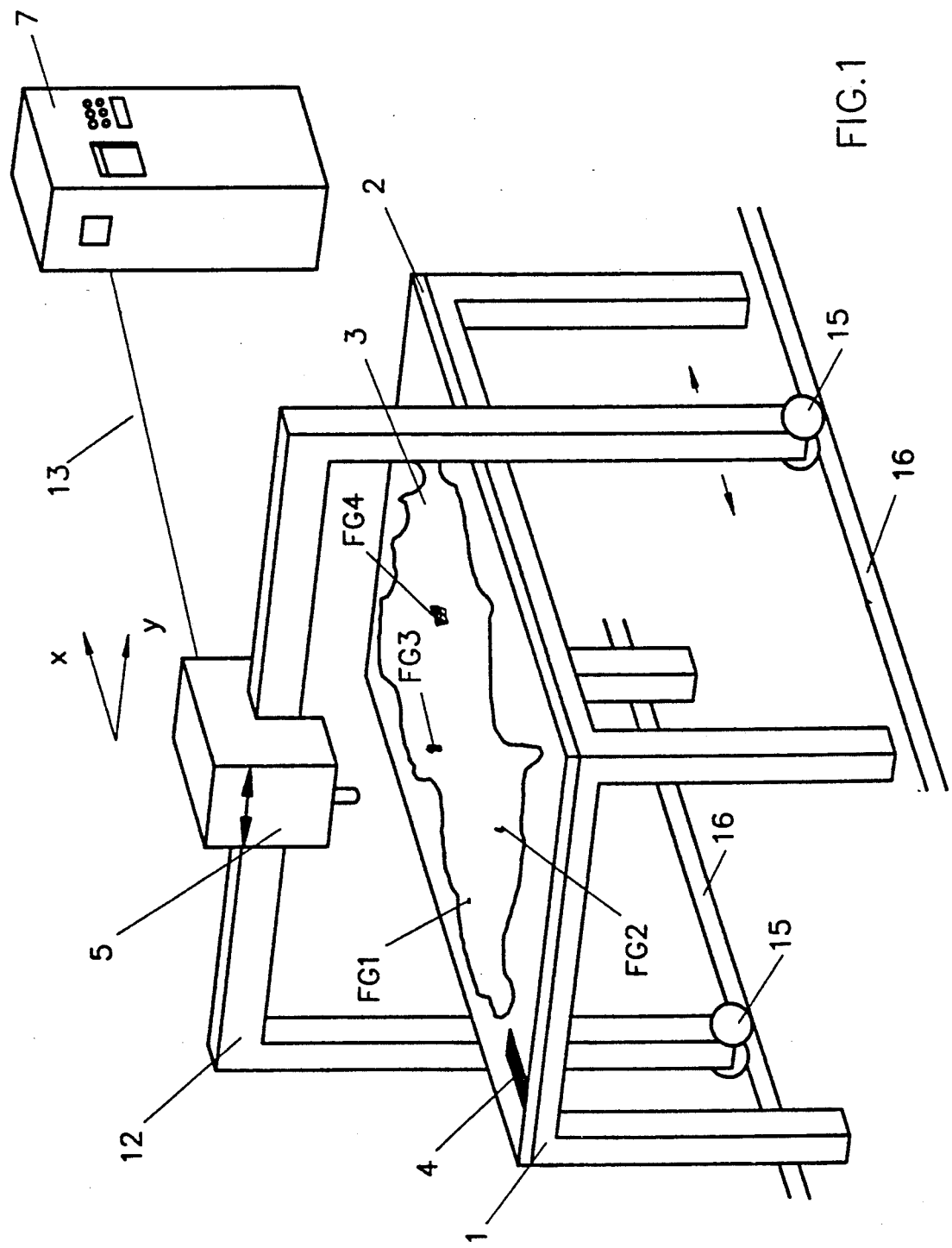
FIG. 1 shows a laying table with an electronic camera arranged above it.

FIG. 1 shows, in diagrammatic form, a laying table 1 with an electronic camera 5 arranged above it. Each individual skin 3 is placed on a pallet 2 which can be received by the laying table 1. The camera 5 is arranged above the laying table and is moveable in transverse direction Y on a support 12 which can be moved in the longitudinal direction X and is connected via a data line 13 with the control unit 7. In known manner, the contours of the skin 3 can be detected and digitized (for instance, by a scanner, not shown). The detected contours of the skin 3 are transmitted to the control unit 7.

The camera 5 is then guided, line by line, over the pallet 2 in order to detect any defects present in the skin 3, advantageously including their locations and sizes Defects FG1, FG2, FG3 and FG4 are shown in FIG. 1. For this purpose, it is important to use a camera 5 which has a high degree of resolution so as to be able to detect even very small defects FG in material or structure. The line-by-line scanning of the skin 3 is effected by moving the support 12 step-by-step in the X direction over rollers 15 which travel on rails 16. The camera 5 preferably moves in the Y-direction while the support 12 is stopped. The drive can be effected by electric motors, not shown in detail, which are controlled by the control unit 7.

The surface of the pallet 2 is advantageously colored so that it forms a good color contrast with the leather skin resting on it. By this feature, in addition to the camera detecting defects, the contour of the skin 3 can also be directly detected and transmitted to the control unit 7, as a result of which the additional use of a scanner can be dispensed with. A contrasting background also advantageously permits a hole to be detected with a color camera, by detecting the background color showing through the hole.

Depending on the degree or magnitude G1, G2, etc., of the detected defects FG1, FG2, FG3, FG4, ... FGmax (scar, tear, small hole, large hole, etc.), the recording of that defect in the camera 5 or transmission to the control unit 7 is represented as a different shade of color, hereinafter "shade", or in the case of a black-and-white camera, by correspondingly graded gray values. The sizes of the defects are also detected.

A color camera can be expected to give better resolution, since it can detect different colors and shades of colors, which can be distinguished better than merely gray values, having distinct color temperatures which are correspondingly far apart.

In other words, the shades that a black-and-white camera can reproduce are white, ..., light gray, ..., dark gray, ..., and black. A color camera, on the other hand, can render the shades light blue, medium blue, and dark blue, or light red, medium red, and dark red, for example.

The color of a defect—a scar, rip, or hole—in a piece of leather differs from that of the surrounding area. Otherwise, the human eye would be unable to detect it A scar that is elevated above the surface of the leather will throw a different kind of shadow than a crack, which is lower than its surroundings. Like the human eye, the camera can represent these defects only as varying shades. When the images of a series of cracks, scars, and other defects are compared, it will be evident that a particular type of defect always has a particular color. This color depends on the type of camera employed. It is conceivable, for instance, for cracks always to show up as white, with scars being gray and holes black.

The classification of defects into levels G1, ..., G4, ... depends on how they affect the aesthetic sensitivity of the observer, considering the final product to be manufactured A scar for example is considered less unpleasing than a crack, a small hole less than a large hole, etc. Assuming that a scar is defined as the lowest level G1 of defect, and if it is known from experience that the camera will represent it as white, every white spot will represent a scar, namely defect level G1.

In the particular case of holes, strictly speaking a small hole may have the same color as a large hole, because that color depends on the background color that shows through the hole. If a degree of defect G3 is assigned to a small hole and degree G4 is assigned to a large hole, the degree of the defect would be assessed not merely from the color per se, but also from the size of the detected spot.

The definition of a degree of defect can be expanded to any extent desired. A level G3 defect for example could be defined to be a simple color variation in the leather, and level G4 could be defined to be a hole, so that various values would be redefined. In the final analysis as many different defect levels can be defined as desired. The camera of course does not detect the defect levels per se. Rather, the defect level G1, G2, etc., to be associated with each color value detected by the camera is prescribed ahead of time.

Camera 5 in the disclosed embodiment is a commercially available video camera. It can be either black-and-white or color For example, the Kodak MEGA-PLUS TM video camera described in the brochure titled KODAK MEGAPLUS TM CAMERA (incorporated by reference) is capable of distinguishing 256 gray levels in a 1.4-million-pixel image and generating a digital or analog output video signal The advantage of a color camera is that it can handle not just shades of gray but also various hues in the leather. Defects of color such as discolored spots are accordingly easier to detect than with a black-and-white camera, since a color camera can detect the actual color deviation. Therefore, various defect levels can be defined in terms of defective hue.

The camera detects essentially what the human eye detects It may detect an artifact colored light gray, dark gray, red, green, etc. In order to properly respond to that artifact, the control unit must be informed ahead of time what sort of structure is represented as light gray, dark gray, red, or green, and what sort of processing of the leather skin should be provided in response to that detected structure.

An example of software that can be used for image processing and can process the 256 different gray levels from a black-and-white camera is sold by BioScan Inc., of Edmonts, Wash. 98020 under the name OPTIMAS, Version 2.03 (incorporated by reference).

Figure 3:
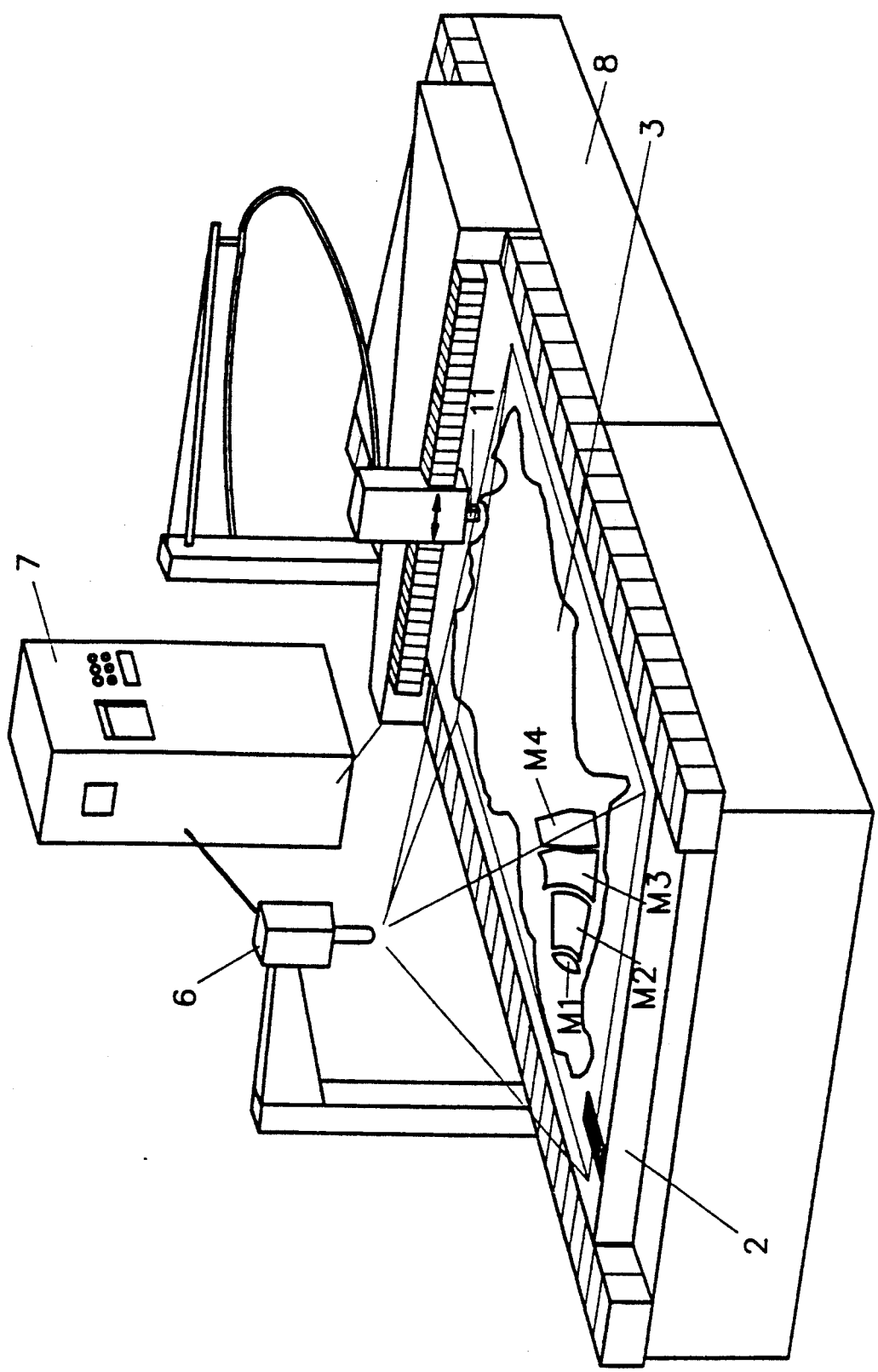
FIG. 3 shows the cutting system of FIG. 2 with a projector arranged above it.
Figure 4A:
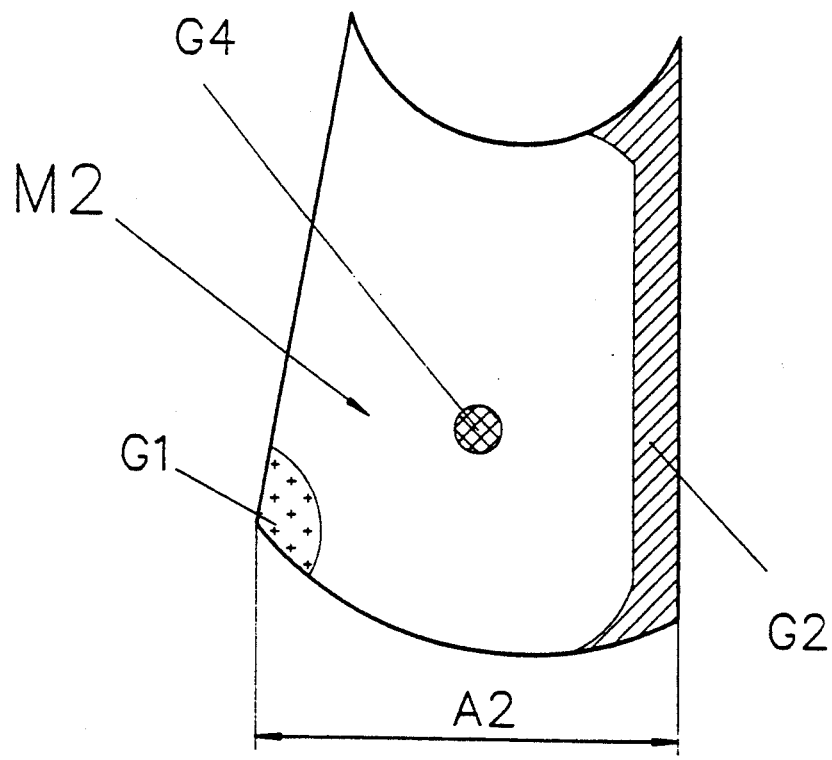
FIGS. 4, 4a show, by way of example, two contours which are to be cut out from a piece of natural leather.
Figure 4:
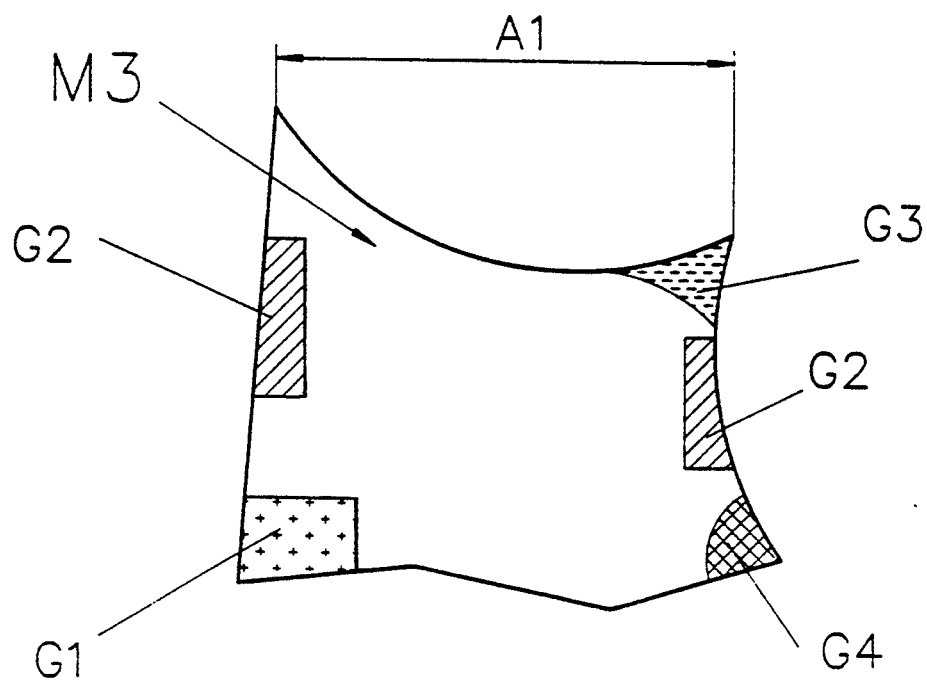

All contours M1, M2, M3, M4 . . . Mmax to be cut from the skin 3 (see FIG. 3) have been previously stored in digital form in the control unit 7. Furthermore, for each individual contour M, areas or regions may be defined where respective ranges of degree of defect (G1, G2, G3, G4 . . . , Gmax) are permissible (FIGS. 4, 4a). The permissible range of degree of defect defines the degree (scar, tear, small hole, large hole, etc.) that a detected defect FG1, . . . FG4 may have, without substantially disturbing the finished part so as to make it unacceptable.

For this purpose, it is given that in each case, given the largest defect Gmax which can be tolerated, lesser degrees of defect can also be tolerated. For instance, the maximum Gmax may be defined as a hole having a given diameter and the minimum defect Gmin may be defined as a scar of a given length In the drawing, the degrees of the illustrated defects are characterized as G1 to G4, G4 representing the maximum degree of defect and G1 the minimum degree of defect.

For example, within the degree of defect range G4 of the contour M, G4 defects as well as all lower degrees of defect G1 to G3 are tolerated, while in the range G1 only the minimum degree of defect G1 is permissible, but not degrees G2 to G4.

For example, when contours are nested on skins for a leather chair, certain areas are designated as not being allowed to include any defects. These areas might later show up on the surface of a cushion or arm, where they would be immediately visible. Scars are definitely tolerable in less obvious areas where they are not directly in sight Edges that will eventually end up inside a seam can even have holes without making any difference. Cracks are tolerable on the bottom of a cushion The areas of a blank that will correspond to given areas of the finished work are known. The extent of prescribed defect ranges is determined by the level of quality a cutting or assembly operation will have to adhere to.

Some sections of the contours M1, M2, M3, . . . can be given additional restrictions. An example of such a restriction is that the fibril matting pattern in section A2 of contour M2 may be constrained to be congruous with that in section A1 of contour M3, because the two contours M2, M3 adjoin here in the finished product In this way, disturbing transitions in structure are avoided This situation is roughly analogous to the example of joining two pieces of striped cloth to make a shirt. When two blanks are sewn together, the stripes in each blank must extend in the same direction at the seam (the pattern must match) so that the final shirt will not have horizontal stripes on the back and vertical stripes on the front. The same phenomenon holds for leather. A particular orientation is prescribed, and maintaining it is a characteristic of high quality.

Waste can also be avoided by requiring adjacent contours to match closely.

After the defects FG, degrees of defect G, sizes, and locations, have been stored in the control unit 7, all possible cutting positions are simulated by means of a suitable computer program in the control unit, for example the program distributed by Dürkopp Adler AG under the trade name DataNEST (incorporated by reference). Such a program simulates all possible combinations and arrangements of the largest possible number of stored contours M, with due consideration of the prerecorded defects FG1 to FGmax and the correspondingly permissible degrees of defect GI to Gmax in the ranges G on the contours M to be cut out. These contours do not exist physically but rather are stored in the form of a family of coordinates in the computer of the control unit 7. After each simulation process, the computer determines the degree of utilization obtained, i.e., the ratio of the total area of the skin to the area of the possible cut-out parts laid out on the skin.

After the skin 3 has been optimally nested by this simulation process, i.e., the maximum possible number of contours M which can be cut out has been determined, the pattern of the cutting layout found is stored in the control unit 7. Each pallet 2, 2', 2" is provided with a different coding 4 (see FIGS. 1 and 5A-5D), for instance a bar code, which can be read by a known reader so that the stored cutting layout is associated with a given code 4 and thus with a specific pallet 2 or skin 3. The pallet 2 with the skin 3 resting on it can then be placed in an intermediate storage space SP (FIGS. 5 and 5B) which, for reasons of efficient manufacture, serves as intermediate storage for skins after nesting of the contours to be cut, until they are to be worked further.

On another pallet 2', which has been suitably marked as already described, nesting is effected on another skin in accordance with the nesting process described above. The number of possible nesting processes is accordingly limited only by the storage capacity of the computer or the spatial conditions of the intermediate storage space SP.

Figure 2:
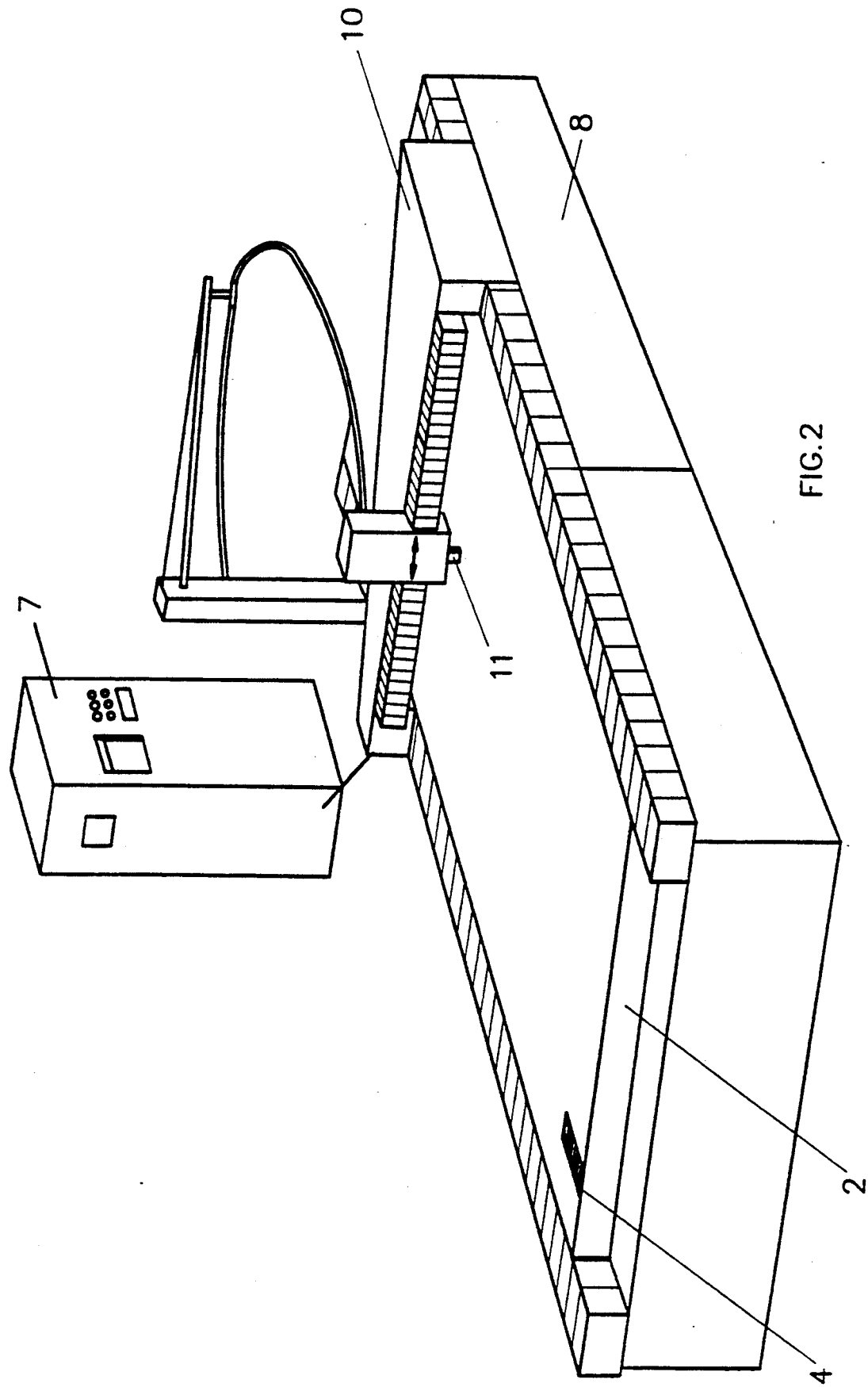
FIG. 2 shows an electronically controlled high-pressure, fluid-jet or laser-beam cutting system.

From the intermediate storage space SP, the pallets 2, 2', 2" are placed on the cutting table 8 of a numerically controlled cutting system, for instance a high-pressure fluid-jet or a laser-beam cutting system (FIG. 2). The coding 4 is detected either by an electronic reader (not shown) or manually and is transmitted to the control unit 7. Similarly, however, it is also possible for the coding 4 of each pallet 2, 2' . . . to be detected and transmitted by the camera 5. In the control unit 7, the corresponding cutting pattern is now selected on the basis of the pallet coding which has been entered and that cutting pattern is used as the cutting program for the cutting system. In other words, the cutting nozzle 11 travels according to the individual contour data M which have been stored during the nesting process.

Figure 5D:
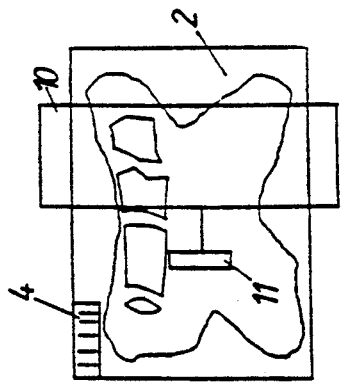
FIGS. 5-5D show diagrammatically a series of individual work stations and operations performed there, from the nesting step to the cutting step, shown in each case in elevation and in top view.
Figure 5C:
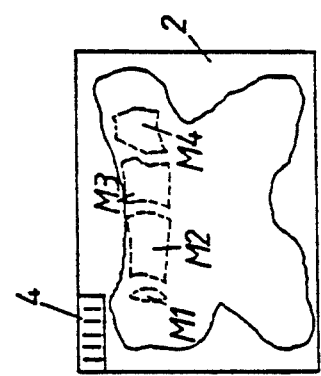
Figure 5B:
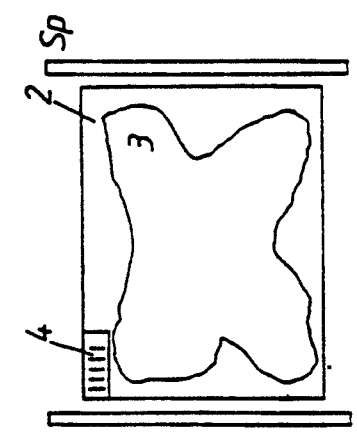
Figure 5A:
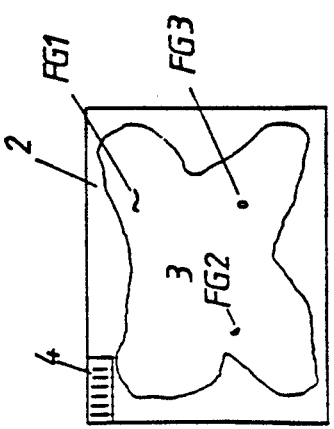

A projection device 6 (FIG. 5) such as, for instance, the one sold by Hughes Aircraft under the name "Graphics Projector 700" (incorporated by reference) may be connected with the electronic control unit 7, and arranged above the work table 8. With this projection device, before the cutting is effected, the cutting program or the position of the cutting pattern can be projected onto the leather and can be visually checked by an experienced operator to make certain that the image of the cutting pattern found in the simulation satisfies all requirements (FIGS. 3, 5, 5C). In this connection, the areas having specific permissible defect degree ranges G1, G2, . . . can also be projected.

The moveable pallet system as well as the intermediate storage space SP can be dispensed with if the cutting region is identical to the layout region and the detection region In that case, the optional visual verification step and the cutting step can take place directly after the nesting process. For this purpose, the camera 5 may be arranged directly on the gantry 10 of the cutting system so as to move with the latter over the cutting table 8.

It is also conceivable to detect the outer contour and the locations of defects in the skin by laser scanning rather than by a camera.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for nesting contours to be cut out of a piece of natural leather comprising the steps of:
   optically detecting the locations and sizes of any defects of the piece of leather automatically, with an automatic optical detection system, such defects being detected by the detection system as a function of varying detected shades of said defects;
   transmitting data representative of such defects and shades to a computer and storing such data therein;
   storing in the computer a plurality of contours corresponding to parts to be cut out of said leather;
   correlating the detected defect-representing shades with respective predefined degrees of said defects;
   defining regions in the stored contours of the parts to be cut out, said regions having respective degree-of-defect ranges, which specify a maximum degree of defect to be accepted in each said region;
   simulating in the computer a plurality of possible arrangements of the contours to be cut out, wherein, in each possible arrangement, only defects within the permissible degree of defect range are present in said defined regions;
   for each simulated arrangement, determining a degree of utilization of said piece of leather;
   comparing the degrees of utilization of said simulated arrangements; and
   after completing the comparison, automatically cutting according to the arrangement with which an optimal degree of utilization has been obtained.

2. A method according to claim 1, further comprising the steps of defining edge associations of the contours with respect to each other, and taking such edge associations into account when determining said possible arrangements.

3. A method according to claim 2, wherein the courses of edges of adjacent contours to be cut out are matched so as to reduce waste of leather material between said contours.

4. A method according to claim 2, wherein grain patterns of said leather within said contours are automatically matched so as to achieve an aesthetically improved transition between said contours.

5. A method according to claim 2, wherein such edge associations are taken into account to associate fibril matting patterns within the respective contours.

6. A method according to claim 1, wherein the optical detection system includes a black-and-white camera.

7. A method according to claim 6, wherein each given degree of defect is defined to include all lower degrees of defect so as to create an acceptance range of the permissible degrees of the detected defects, whereby the acceptance range includes all lower and equal degrees of defect.

8. A method according to claim 1, wherein the optical detection system includes a color camera.

9. A method according to claim 8, wherein different degrees of defect are associated with different shades of detected color.

10. A method according to claim 9, wherein each color corresponding to a given degree of defect is defined to include all colors corresponding to lower degrees of defect, so as to create an acceptance range (Gmax>G4>G3> . . . >G1) of the permissible degrees of the detected defects (FG1, . . . , FGmax), whereby the degree of defect (Gn) permissible in each case includes all lower and equal degrees of defect (G1, . . . , Gn-1, Gn).

11. A method according to claim 1, wherein the optical detection system includes a laser scanner which detects the defects.

* * * * *